(12) United States Patent
Greenfield et al.

(10) Patent No.: US 11,244,742 B2
(45) Date of Patent: Feb. 8, 2022

(54) SYSTEM FOR GENERATING GENOMICS DATA, WITH ADJUSTED QUALITY SCORES, AND DEVICE, METHOD, AND SOFTWARE PRODUCT FOR USE THEREIN

(71) Applicant: Petagene Ltd., Cambridge (GB)

(72) Inventors: Daniel Leo Greenfield, Cambridge (GB); Alban Rrustemi, Cambridge (GB)

(73) Assignee: Petagene Ltd., Cambridge (GB)

( * ) Notice: Subject to any disclaimer, the term of this patent is extended or adjusted under 35 U.S.C. 154(b) by 792 days.

(21) Appl. No.: 15/766,305

(22) PCT Filed: Oct. 6, 2016

(86) PCT No.: PCT/EP2016/025106
§ 371 (c)(1),
(2) Date: Apr. 5, 2018

(87) PCT Pub. No.: WO2017/059964
PCT Pub. Date: Apr. 13, 2017

(65) Prior Publication Data
US 2019/0121942 A1 Apr. 25, 2019

(30) Foreign Application Priority Data
Oct. 6, 2015 (GB) .................... 1517663

(51) Int. Cl.
*G16B 50/00* (2019.01)
*G16B 30/00* (2019.01)
(Continued)

(52) U.S. Cl.
CPC .......... *G16B 50/00* (2019.02); *G06K 9/6215* (2013.01); *G16B 30/00* (2019.02); *G16B 40/00* (2019.02); *G16B 40/30* (2019.02)

(58) Field of Classification Search
CPC ........ G16B 50/50; G16B 99/00; G16B 50/00; G16B 40/00; G16B 40/30; G16B 30/00; G06K 9/6215
See application file for complete search history.

(56) References Cited

U.S. PATENT DOCUMENTS 9,847,791 B2* 12/2017 Greenfield .............. H03M 7/30
2011/0004413 A1* 1/2011 Carnevali .............. G16B 30/20
702/19
(Continued)

FOREIGN PATENT DOCUMENTS

| CN | 103186716 A | 7/2013 |
| WO | WO 2011/143231 A2 | 11/2011 |
| WO | WO 2014/081882 A2 | 5/2014 |

OTHER PUBLICATIONS

DePristo, M.A., Banks, E., Poplin, R., Garimella, K.V., Maguire, J.R., Hartl, C., Philippakis, A.A., Del Angel, G., Rivas, M.A., Hanna, M. and McKenna, A., 2011. A framework for variation discovery and genotyping using next-generation DNA sequencing data. Nature genetics, 43(5), p. 491. (Year: 2011).*
(Continued)

*Primary Examiner* — Jesse P Frumkin
(74) *Attorney, Agent, or Firm* — Wolf, Greenfield & Sacks, P.C.

(57) ABSTRACT

Techniques for generating output genomics data. The techniques include: receiving a genome sequence read comprising at least one sequence of bases and associated quality scores; and processing the genome sequence read to generate the output genomics data at least in part by: performing a search of the at least one sequence of bases in a reference genome corpus comprising n-mers from a reference genome, based upon a similarity criterion; calculating an adjustment for one or more of the associated quality scores, based upon results of the search, the adjustment calculation
(Continued)

for a quality score associated with a base in the genome sequence read utilising a Bayesian estimation of a likelihood of a sequencing error at the base given the sequence of the read, the Bayesian estimation utilising the results of the search; and adjusting one or more of the associated quality scores according to the calculated adjustment.

22 Claims, 9 Drawing Sheets

(51) Int. Cl.
    *G06K 9/62* (2006.01)
    *G16B 40/00* (2019.01)
    *G16B 40/30* (2019.01)

(56) References Cited

U.S. PATENT DOCUMENTS

| | | | |
|---|---|---|---|
| 2014/0309944 | A1 | 10/2014 | Van Rooyen et al. |
| 2016/0357812 | A1* | 12/2016 | Greenfield ........ G06F 16/24553 |
| 2017/0061072 | A1* | 3/2017 | Kermani ................ G16B 30/00 |
| 2017/0147597 | A1* | 5/2017 | Leighton ................ G16C 99/00 |
| 2018/0101547 | A1* | 4/2018 | Greenfield ............ G06F 16/278 |

OTHER PUBLICATIONS

Yu, Y. William, Deniz Yorukoglu, and Bonnie Berger. "Traversing the k-mer landscape of NGS read datasets for quality score sparsification." In International Conference on Research in Computational Molecular Biology, pp. 385-399. Springer, Cham, 2014. (Year: 2014).*

Kao, Wei-Chun, Kristian Stevens, and Yun S. Song. "BayesCall: A model-based base-calling algorithm for high-throughput short-read sequencing." Genome research 19, No. 10 (2009): 1884-1895. (Year: 2009).*

Combined Search and Examination Report for United Kingdom Application No. GB 1517663.9 dated Nov. 24, 2015.

Extended European Search Report for European Application No. EP 16020181.0 dated Sep. 14, 2016.

International Search Report and Written Opinion for International Application No. PCT/EP2016/025106 dated Jan. 11, 2017.

Search Report for United Kingdom Application No. GB 1508314.0 dated Oct. 19, 2016.

Chung et al., Using geometric structures to improve the error correction algorithm of high-throughput sequencing data on MapReduce framework. 2014 IEEE International Conference on Big Data (Big Data). Oct. 27, 2014;784-789.

Depristo et al., A framework for variation discovery and genotyping using next-generation DNA sequencing data. Nature genetics. May 2011;43(5):491-498.

Greenfield et al., GeneCodeq: quality score compression and improved genotyping using a Bayesian framework. Bioinformatics. Oct. 15, 2016;32(20):3124-32.

Navarro, A guided tour to approximate string matching. ACM computing surveys (CSUR). Mar. 1, 2001;33(1):31-88.

Yu et al., Traversing the k-mer landscape of NGS read datasets for quality score sparsification. International Conference on Research in Computational Molecular Biology. Apr. 2, 2014:385-399.

* cited by examiner

SYSTEM FOR GENERATING GENOMICS DATA, WITH ADJUSTED QUALITY SCORES, AND DEVICE, METHOD, AND SOFTWARE PRODUCT FOR USE THEREIN

CROSS-REFERENCE TO RELATED APPLICATIONS

This application is a national stage filing under 35 U.S.C. § 371 of International Patent Application Serial No. PCT/EP/2016/025106, filed Oct. 6, 2016, which claims priority to United Kingdom application number 1517663.9, filed Oct. 6, 2015. The entire contents of these applications are incorporated herein by reference in their entirety.

TECHNICAL FIELD

The present disclosure relates to systems for generating genomics data, for example to systems including apparatus for generating primary genomics data from a biological sample, and a data processing arrangement for transforming the primary genomics data into secondary genomics data, wherein the secondary genomics data has a lower error occurrence therein in comparison to the primary genomics data. Moreover, the present disclosure relates to devices including a data processing arrangement for processing the primary genomics data to generate the secondary genomics data. Furthermore, the present disclosure relates to methods of transforming the primary genomic data to generate the secondary genomics data. Additionally, the present disclosure relates to software products recorded on machine readable data storage media, wherein the software products are executable on computing hardware for implementing aforesaid methods. In addition, the invention relates to a device arranged capable of implementing the aforementioned methods. The present disclosure concerns, for example, a method of transforming the primary genomics data to adjust quality score values of the primary genomic data which is generated by genomic sequencing, for example using gene splicing methods and electrophoresis measurements. Thus, more specifically, the present disclosure concerns a method to refine high throughput sequencing quality score information obtained via next generation sequencing technologies.

BACKGROUND

DNA (deoxyribonucleic acid) molecules carry genetic instructions. Such molecules carry most of the genetic instructions used by organisms for their development, for their vital metabolic functioning and for their reproduction. DNA molecules consist of two biopolymer strands coiled around each other in a double helix structure. Each strand includes a chain of units called nucleotides; the nucleotides can be of four mutually different types, namely adenine (A), guanine (G), cytosine (C) and thymine (T). In genomics, these nucleotides are often referred to as "bases". Due to the paired strand structure of the DNA molecule, such bases are often encountered as base-pairs. Determining an order of bases in a given DNA molecule is achieved by a technique known as "sequencing"; this technique has become a key tool in contemporary biological research and in medicine.

Different DNA sequencing techniques have been developed over the years, since such techniques first became known in the early 1970's. As the techniques have progressed as a function of time, faster and more accurate sequencing results have been obtained as a result. Such progressed techniques have resulted in growing volumes of sequencing data, and methods have been developed to handle such sequencing data in a useful manner. Equipment, for example NGS sequencing machines, capable of performing DNA sequencing operations is now more widely available, and is manufactured by companies such as Illumina Inc., for example. Such equipment investigates samples of materials, wherein the samples include genetic information strands, for example DNA molecules, that have been chopped into pieces, wherein each piece often comprises a length of hundreds of bases, or base pairs. These pieces are referred to as "genome sequence reads" or, simply, "reads" or "Reads". Each piece is then processed to determine its genetic content, and corresponding genetic content data, namely "results", are then output as a list of reads. A majority of genetic content data produced by aforementioned NGS sequencing machines consists of such reads, where each base is associated with a corresponding quality value, also referred to as a "quality score". The quality score represents an estimate of a probability that a given base has been sensed correctly or, alternatively, incorrectly; in other words, the quality score is a measure of an analogous technical "signal-to-noise ratio" (SNR) of the equipment. Normally, the quality score is encoded in the genetic content data using a Phred scale, also known as "Phred scores", which is a widely accepted and used quality indicator generated by a base caller during a process of sequencing genetic information from biological genetic samples, and comprise a measure of the quality of identification of bases. Quality scores are used for a variety of tasks including:

(i) assessment of the sequence quality;
(ii) filtering low-quality reading of a sample sequence;
(iii) assembling genome sequences; and
(iv) mapping reads to reference sequences and implementing accurate genotyping.

In addition to base information and corresponding quality scores, aforementioned NGS sequencing machines potentially also produce metadata corresponding to sequence reads, for example "read identifiers". Further processing of the resulting NGS data is then usually implemented offline on a computing device or other such data analysis tool. In practice, genomic sequencing data, including the aforesaid quality score, is potentially considerable in volume, for example approaching 1 TeraBytes.

Genomics data potentially comprises sequencing data, assembly and analysis data, as well as information regarding a manner of functioning and a structure of genomes. Developments in genetic sequencing techniques have allowed data pertaining to reference genomes to be produced, each aiming to represent a complete DNA sequence, for a given species. In particular, one important example is the human species. However, genomic sequencing techniques can be applied to DNA material, regardless of species origin, as all species employ DNA as a way of transferring biological information from one generation of a given species to a subsequent generation. Contemporary methods of DNA sequencing rely on reference genomes for determining possible positions of sequenced pieces within the entire DNA molecule; various correlation algorithms have been hitherto employed for determining such possible positions.

Contemporary known developments in DNA sequencing include an introduction of high throughput sequencing (HTS), which has accelerated the process of sequencing and thereby improved overall acquisition of genetic data. Over the past decade, unprecedented advances in next generation sequencing (NGS) technologies have reduced the cost of sequencing by a factor of 10,000. Sequencing with NGS produces a large data footprint for each individual genome. With NGS becoming more widely adopted, storing and transferring raw sequencing information is becoming prohibitively expensive, necessitating efficient methods of handling of data thereby obtained.

Genetic sequencing data stored, for example, on a computer disk, frequently in a compressed form, comprise both base read data from sequencing operations and quality score values associated with each base read. When compared to the read sequence data, quality score values contribute to a majority of the genetic sequencing data stored on the disk in compressed form. Such a large proportion of the data being quality score values can be attributed to a larger associated alphabet required for expressing such quality scores, as well as to an intrinsically higher entropy of the data. Quality score information often takes up more than twice the space of the sequence data information. Lossless compression algorithms and entropy encoders are reaching their theoretical limits, defined by Shannon's Theory, and delivering only moderate compression ratios. Lossy compression schemes are often considered, but their adoption has been limited due to concerns about potential loss of valuable information. Consequently, there is a need for a more efficient compression of raw data generated by sequencing machines. Thus, there arises a need for genetic sequencing equipment which is operable to determine from biological genetic material corresponding genetic sequencing data in a form that results in smaller data quantities being generated. As conventional compression techniques have reached a limit to their theoretical potential, an alternative approach to improving equipment performance is therefore required.

SUMMARY

The present disclosure seeks to provide an improved system for generating genomics data from biological genetic material.

Moreover, the present disclosure seeks to provide a device for use in the aforesaid improved system for reducing a size of genetic sequencing data that is generated in operation by the aforesaid improved system.

Furthermore, the present disclosure seeks to provide an improved method of generating genomics data from biological genetic material.

Additionally, the present disclosure seeks to provide, for example for use in the aforesaid improved system, an improved method of transforming quality scores of bases in genome sequences, in order to improve a quality of the quality scores, thereby enabling a quantity of genomics data to be reduced.

According to a first aspect, there is provided a system for generating output genomics data from biological genetic material, wherein the system includes:
(i) a genetic reading apparatus which is operable to read bases included in the biological genetic material to generate a genome sequence read, wherein the genome sequence read comprises at least one sequence of bases and associated quality scores; and
(ii) a data processing apparatus for processing the genome sequence read to generate the output genomics data, characterized in that the data processing apparatus is operable:
(a) to determine similarity criteria for performing searching in a reference genome corpus;
(b) to perform a search of the at least one sequence of bases in the reference genome corpus, based upon the similarity criteria;
(c) to calculate an adjustment for one or more of the associated quality scores, based upon results of the search; and
(d) to adjust one or more of the associated quality scores according to the calculated adjustment from (c).

The system, and its associated method of operation, are capable of improving genotyping accuracy of sequence data derived from biological genetic material.

Moreover, the system, and its associated method of operation, are capable of substantially increasing quality score compressibility of genomic data and concurrently improve genotyping accuracy of the corresponding sequence data. The improvement of quality score values, according to evidence available in initial sequence data, leads to significantly higher compressibility of genomic data, and reduces a required storage space to store the genomic data in compressed form.

Optionally, in operation of the system, the similarity criteria includes a correspondence distance based upon a number of bases that are different between portions of the reference genome corpus and the at least one sequence of bases.

Optionally, in operation of the system, the adjustment comprises an improvement to the quality scores. More optionally, in operation of the system, the improvement to the quality scores is performed up to a pre-determined maximum.

Optionally, in operation of the system, the correspondence distance to search is based upon a Hamming-distance or Edit-distance search.

Optionally, in operation of the system, the adjustment calculation utilises a Bayesian estimation of a likelihood of a sequencing error for a corresponding base of one or more of the quality scores in the genome sequence read, wherein the Bayesian estimation utilises the results of the search.

Optionally, in operation of the system, the adjustment calculation utilises at least one of the associated quality scores of the genome sequence read.

Optionally, in operation of the system, the adjustment calculation utilises estimations of a mutation between the reference genome corpus and a sample underlying the genome sequence read.

Optionally, in operation of the system, the reference genome corpus includes at least a portion from one reference genome for the genome sequence read. Optionally, in operation of the system, the reference genome corpus includes a collection of sequences of DNA and/or RNA.

Optionally, the system is further operable:
(i) to pre-select at least one success criterion, suitable for determining whether or not adjustments to quality scores of said genome sequence read are sufficient;
(ii) to calculate at least one candidate adjustment for quality scores of the genome sequence read;
(iii) to determine if the pre-selected at least one success criterion has been met;
(iv) if the adjusted quality scores of the genome sequence read do not meet the pre-selected at least one success criterion, to perform given steps using different success criteria;
(v) if the adjusted quality scores of the genome sequence read meet the pre-selected at least one success criterion, to adjust the quality scores according to the calculation.

Optionally, the system is operable to perform the search, wherein the data processing apparatus is operable:

(i) to partition the sequence of bases into a plurality of slots;
(ii) to perform at least one lookup operation for at least one slot into the reference genome corpus to obtain one or more candidate codewords; and
(iii) to combine candidate codewords from the at least one slot to obtain a list of results.

Optionally, in operation of the system, the data processing apparatus is operable to perform partitioning by utilizing a Pigeonhole Principle.

Optionally, in operation of the system, the data processing apparatus is operable to filter the list of results so as to exclude those not within the similarity criteria to search.

Optionally, in operation of the system, the slots comprise a fixed width or a variable width. More optionally, in operation of the system, the slots are within a pre-determined range. More optionally, in operation of the system, slots are within a range from 11 to 32 bases.

Optionally, in operation of the system, the at least one lookup operation is performed as part of the search by utilising an index of codewords within the reference genome corpus.

Optionally, in operation of the system, the data processing apparatus is further operable:
(a) to arrange the index to comprise a primary index;
(b) to partition the at least one slot into a fixed-width primary search key and non-fixed width secondary search key during the at least one lookup operation;
(C) to perform a primary lookup by utilising the fixed-width primary search key in the primary index to obtain primary search results; and
(d) to perform a secondary lookup based on the primary search results, using the secondary search key.

More optionally, in operation of the system, the secondary lookup utilises a binary traversal of sorted values to find matching candidate results.

According to a second aspect, there is provided a device for generating output genomics data from biological genetic material, characterized in that the device is operable:
(i) to receive a genome sequence read from a genetic reading apparatus which is operable to read bases included in the biological genetic material to generate the genome sequence read, wherein the genome sequence read comprises at least one sequence of bases and associated quality scores; and
(ii) to process the genome sequence read to generate the output genomics data,
characterized in that the device is operable:
(a) to determine similarity criteria for performing searching in a reference genome corpus;
(b) to perform a search of the at least one sequence of bases in the reference genome corpus, based upon the similarity criteria;
(c) to calculate an adjustment for one or more of the associated quality scores, based upon results of the search; and
(d) to adjust one or more of the associated quality scores according to the calculated adjustment from (c).

Optionally, in operation of the device, the similarity criteria includes a correspondence distance based upon a number of bases that are different between portions of the reference genome corpus and the at least one sequence of bases.

Optionally, in operation of the device, the adjustment comprises an improvement to the quality scores. More optionally, in operation of the device, the improvement to the quality scores is performed up to a pre-determined maximum.

Optionally, in operation of the device, the correspondence distance to search is based upon a Hamming-distance or Edit-distance search.

Optionally, in operation of the device, the adjustment calculation utilises a Bayesian estimation of a likelihood of a sequencing error for a corresponding base of one or more of the quality scores in the genome sequence read, wherein the Bayesian estimation utilises the results of the search.

Optionally, in operation of the device, the adjustment calculation utilises at least one of the associated quality scores of the genome sequence read.

Optionally, in operation of the device, the adjustment calculation utilises estimations of a mutation between the reference genome corpus and a sample underlying the genome sequence read.

Optionally, in operation of the device, the reference genome corpus includes at least one reference genome for the genome sequence read.

Optionally, the device is further operable:
(i) to pre-select at least one success criterion, suitable for determining whether or not adjustments to quality scores of said genome sequence read are sufficient;
(ii) to calculate at least one candidate adjustment for quality scores of the genome sequence read;
(iii) to determine if the pre-selected at least one success criterion has been met;
(iv) if the adjusted quality scores of the genome sequence read do not meet the pre-selected at least one success criterion, to perform given steps using different success criteria;
(v) if the adjusted quality scores of the genome sequence read meet the pre-selected at least one success criterion, to adjust the quality scores according to the calculation.

Optionally, the device is operable to perform the search, wherein the device is operable:
(i) to partition the sequence of bases into a plurality of slots;
(ii) to perform at least one lookup operation for at least one slot into the reference genome corpus to obtain one or more candidate codewords; and
(iii) to combine candidate codewords from the at least one slot to obtain a list of results.

Optionally, the device is operable to perform partitioning by utilizing a Pigeonhole Principle.

Optionally, the device is operable to filter the list of results so as to exclude those not within the similarity criteria to search.

Optionally, in operation of the device, the slots comprise a fixed width or a variable width. More optionally, in operation of the device, the slots are within a pre-determined range. More optionally, in operation of the device, the slots are within a range from 11 to 32 bases.

Optionally, in operation of the device, the at least one lookup operation is performed as part of the search by utilising an index of codewords within the reference genome corpus.

Optionally, the device is further operable:
(a) to arrange the index to comprise a primary index;
(b) to partition the at least one slot into a fixed-width primary search key and non-fixed width secondary search key during the at least one lookup operation;
(c) to perform a primary lookup by utilising the fixed-width primary search key in the primary index to obtain primary search results; and
(d) to perform a secondary lookup based on the primary search results, using the secondary search key.

Optionally, in operation of the device, the secondary lookup utilises a binary traversal of sorted values to find matching candidate results.

According to a third aspect, there is provided a method of generating output genomics data from biological genetic material, wherein the method includes:
(i) using a genetic reading apparatus to read bases included in the biological genetic material to generate a genome sequence read, wherein the genome sequence read comprises at least one sequence of bases and associated quality scores; and
(ii) using a data processing apparatus to process the genome sequence read to generate the output genomics data,
characterized in that the method further comprises:
(a) determining similarity criteria for performing searching in a reference genome corpus;
(b) performing a search of the at least one sequence of bases in the reference genome corpus, based upon the similarity criteria;
(c) calculating an adjustment for one or more of the associated quality scores, based upon results of the search; and
(d) adjusting one or more of the associated quality scores according to the calculated adjustment from (c).

Optionally, when implementing the method, the similarity criteria includes a correspondence distance based upon a number of bases that are different between portions of the reference genome corpus and the at least one sequence of bases.

Optionally, when implementing the method, the adjustment comprises an improvement to the quality scores. More optionally, when implementing the method, the improvement to the quality scores is performed up to a pre-determined maximum.

Optionally, when implementing the method, the correspondence distance to search is based upon a Hamming-distance or Edit-distance search.

Optionally, when implementing the method, the adjustment calculation utilises a Bayesian estimation of a likelihood of a sequencing error for a corresponding base of one or more of the quality scores in the genome sequence read, wherein the Bayesian estimation utilises the results of the search.

Optionally, when implementing the method, the adjustment calculation utilises at least one of the associated quality scores of the genome sequence read.

Optionally, when implementing the method, the adjustment calculation utilises estimations of a mutation between the reference genome corpus and a sample underlying the genome sequence read.

Optionally, when implementing the method, the reference genome corpus includes at least one reference genome for the genome sequence read.

Optionally, the method further includes:
(i) pre-selecting at least one success criterion, suitable for determining whether or not adjustments to quality scores of said genome sequence read are sufficient;
(ii) calculating at least one candidate adjustment for quality scores of the genome sequence read;
(iii) determining if the pre-selected at least one success criterion has been met;
(iv) if the adjusted quality scores of the genome sequence read do not meet the pre-selected at least one success criterion, performing given steps using different success criteria;
(v) if the adjusted quality scores of the genome sequence read meet the pre-selected at least one success criterion, adjusting the quality scores according to the calculation.

Optionally, the method includes performing the search, wherein the search includes:
(i) partitioning the sequence of bases into a plurality of slots;
(ii) performing at least one lookup operation for at least one slot into the reference genome corpus to obtain one or more candidate codewords; and
(iii) combining candidate codewords from the at least one slot to obtain a list of results.

More optionally, the method includes performing partitioning by utilizing a Pigeonhole Principle.

Optionally, the method includes filtering the list of results so as to exclude those not within the similarity criteria to search.

Optionally, when implementing the method, the slots comprise a fixed width or a variable width. More optionally, when implementing the method, the slots are within a pre-determined range. More optionally, when implementing the method, the slots are within a range from 11 to 32 bases.

Optionally, when implementing the method, the at least one lookup operation is performed as part of the search by utilising an index of codewords within the reference genome corpus.

Optionally, the method further includes:
(a) arranging the index to comprise a primary index;
(b) partitioning the at least one slot into a fixed-width primary search key and non-fixed width secondary search key during the at least one lookup operation;
(c) performing a primary lookup by utilising the fixed-width primary search key in the primary index to obtain primary search results; and
(d) performing a secondary lookup based on the primary search results, using the secondary search key.

Optionally, when implementing the method, the secondary lookup utilises a binary traversal of sorted values to find matching candidate results.

According to a fourth aspect, there is provided a system for generating output genomics data from biological genetic material, wherein the system includes:
(i) a genetic reading apparatus which is operable to read bases included in the biological genetic material to generate a genome sequence read, wherein the genome sequence read comprises at least one sequence of bases and associated quality scores; and
(ii) a data processing apparatus for processing the genome sequence read to generate the output genomics data,
characterized in that the data processing apparatus is operable:
(a) to perform a search of the at least one sequence of bases in the reference genome corpus;
(b) to calculate an adjustment for one or more of the associated quality scores, based upon results of the search; and
(c) to adjust one or more of the associated quality scores according to the calculated adjustment from (b).

According to a fifth aspect, there is provided a method of processing genomics data, wherein the method includes:
(i) using a data processing apparatus to process the genome sequence read to generate the output genomics data,
characterized in that the method further comprises:
(a) to perform a search of the at least one sequence of bases in the reference genome corpus;
(b) to calculate an adjustment for one or more of the associated quality scores, based upon results of the search; and
(c) to adjust one or more of the associated quality scores according to the calculated adjustment from (b).

According to a sixth aspect, there is provided a computer program product comprising a non-transitory computer-readable storage medium having computer-readable instructions stored thereon, the computer-readable instructions being executable by a computerized device comprising processing hardware to execute the method pursuant to the third aspect or to execute the method pursuant to the fifth aspect.

In embodiments of the present disclosure, an approach incorporating insights from Coding Theory is used to boost the signal of bases in High Throughput Sequencing (HTS) outputs according to a conservative prior and Bayesian model. Resultant boosted quality scores thereby obtained are a more accurate representation of the confidence of base calls in each Read, and can be better compressed; in other words, such an approach represents an improvement in signal-to-noise ratio (SNR) of the aforementioned improved system when investigating biological genetic material, and is clearly a technical effect in what is essentially a chemical sensing system. Unlike lossy compression schemes that approximate or throw out quality score information, the quality scores from approaches employed in embodiments of the present disclosure are boosted according to a robust and conservative Coding Theory model. A side-effect in embodiments of the present disclosure is that most quality scores are pushed beyond their saturation point of the aforementioned Phred scheme, resulting in high compression ratios being achieved when processing data generated in the aforementioned improved system. Importantly, this Bayesian approach does not modify the quality scores of bases, unless there is a robust statistical basis for doing so. Instead, it improves the underlying quality score of the HTS data under a conservative prior, with improved compression as a side-effect; there is thereby provided a useful technical synergy effect.

In an ordinary case, conventional Coding Theory, for example based on Shannon's Theory, describes how it is feasible to communicate codewords over a noisy communication channel to recover the original codeword. Applying Coding Theory allows for practically separating out signal from noise utilising a Bayesian approach. A Hamming Distance is used to determine a likelihood, in a signal received at a receiver, how one given codeword versus another codeword. The larger the Hamming Distance between all other codewords, the more likely it is that the given codeword can be recovered at the receiver and separated from noise, for example stochastic noise. Indeed, the ability to separate the given codeword from noise at the receiver grows exponentially with its Hamming Distance to other codewords. When applying Coding Theory to boost the signal of bases in HTS outputs, in addition to Hamming Distance, Edit Distance, including Minimum Edit Distance, can be used in embodiments of the present disclosure. Edit distance better captures modifications that result from both genomic mutations and sequencing errors. Further elaboration on these types of distances can be found in: *ACM Computing Surveys*, Vol. 33, No. 1, March 2001, pp. 31-88 (titled, *A Guided Tour to Approximate String Matching*).

DESCRIPTION OF THE DIAGRAMS

Embodiments of the present disclosure will now be described, by way of example only, with reference to the following diagrams wherein.

Figure 3A:
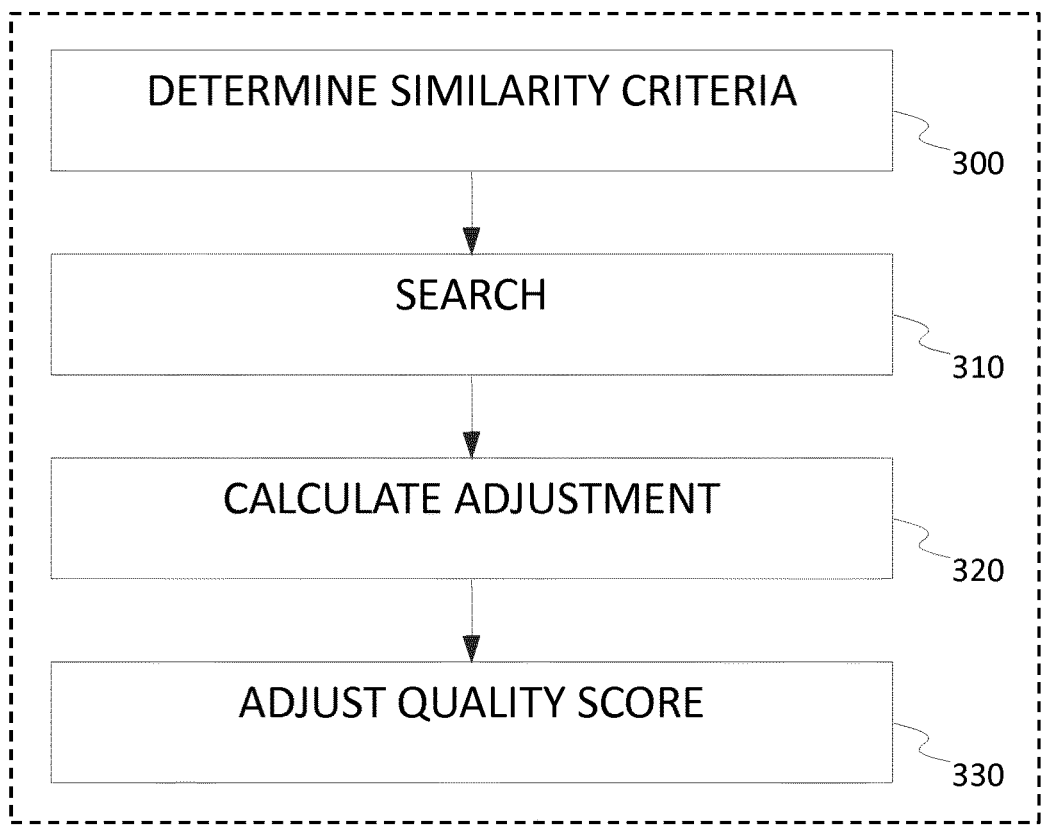
Figure 3B:
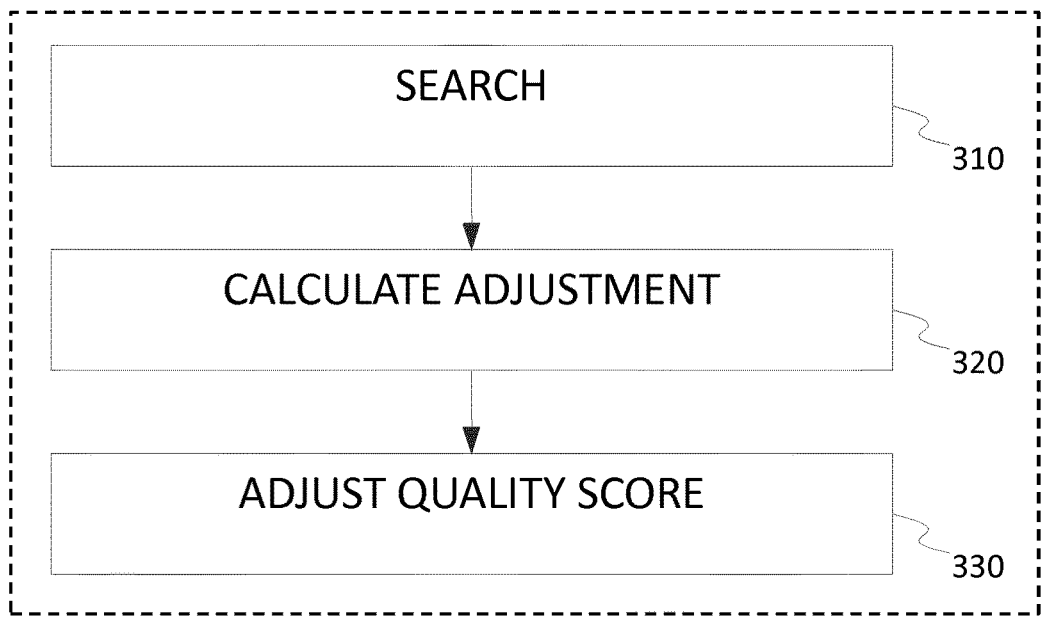
Figure 4A:
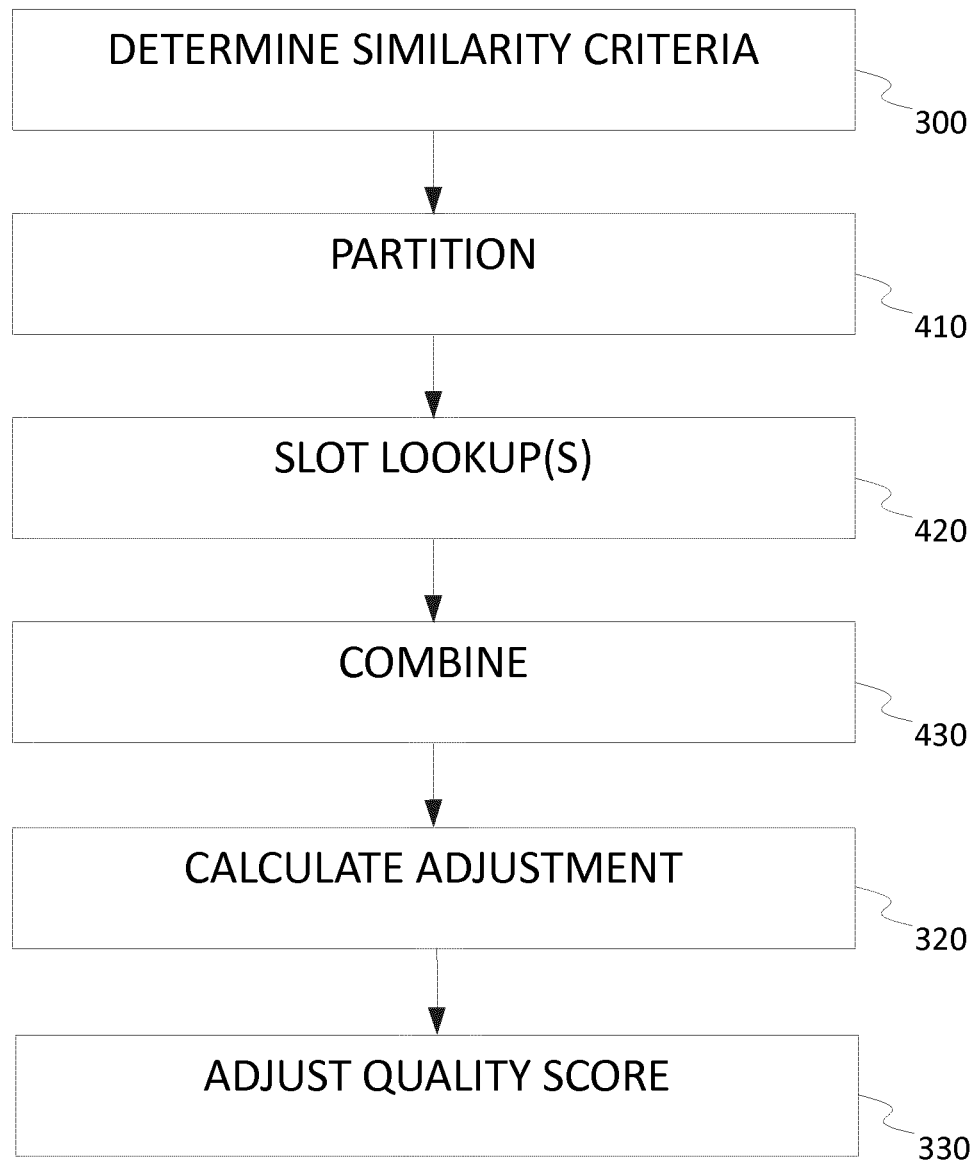
Figure 4B:
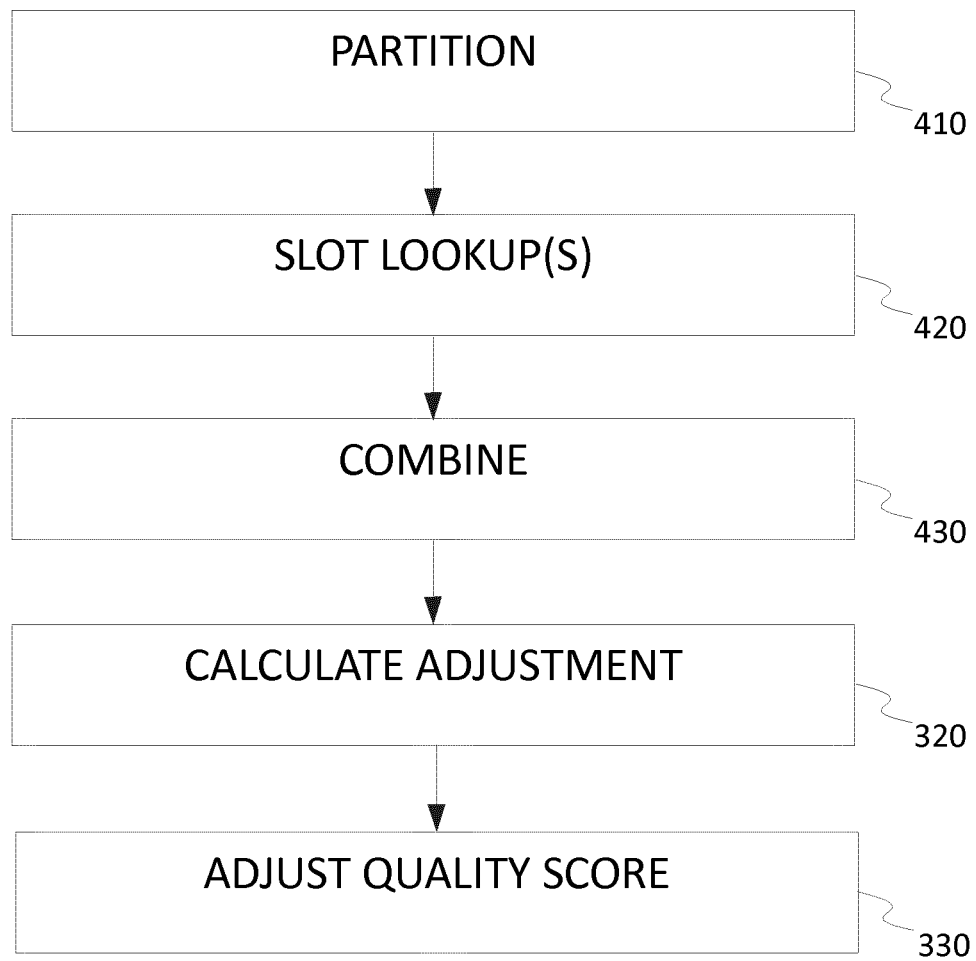

FIG. 3a and FIG. 3b are schematic illustrations of a method according to one embodiment of the present disclosure; FIG. 4a and FIG. 4b are schematic illustrations of a method according to another embodiment of the present disclosure; FIG. 4b illustrates a revised version of method as illustrated in FIG. 4a, whereby step 300 is not incorporated.

Figure 5A:
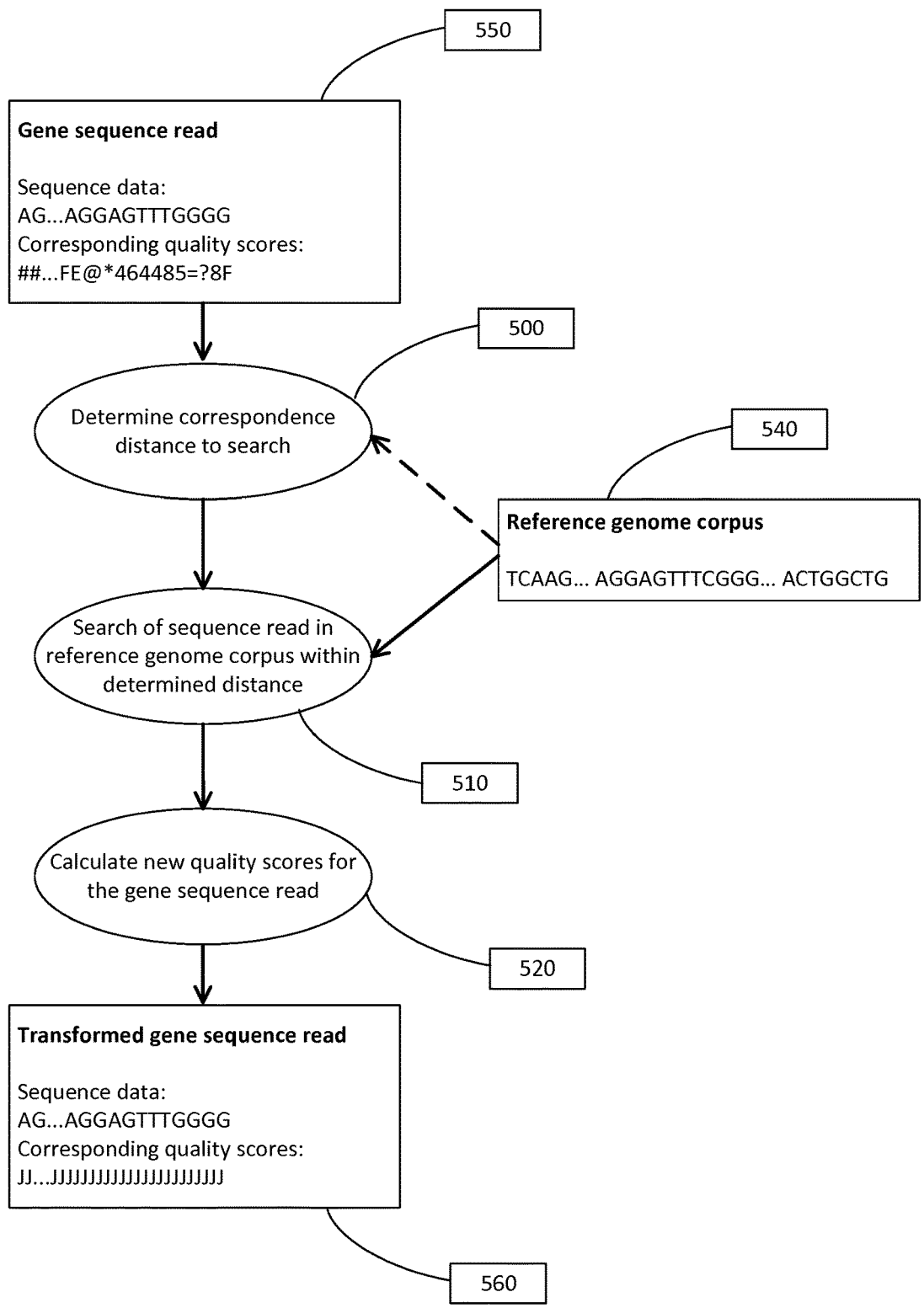
Figure 5B:
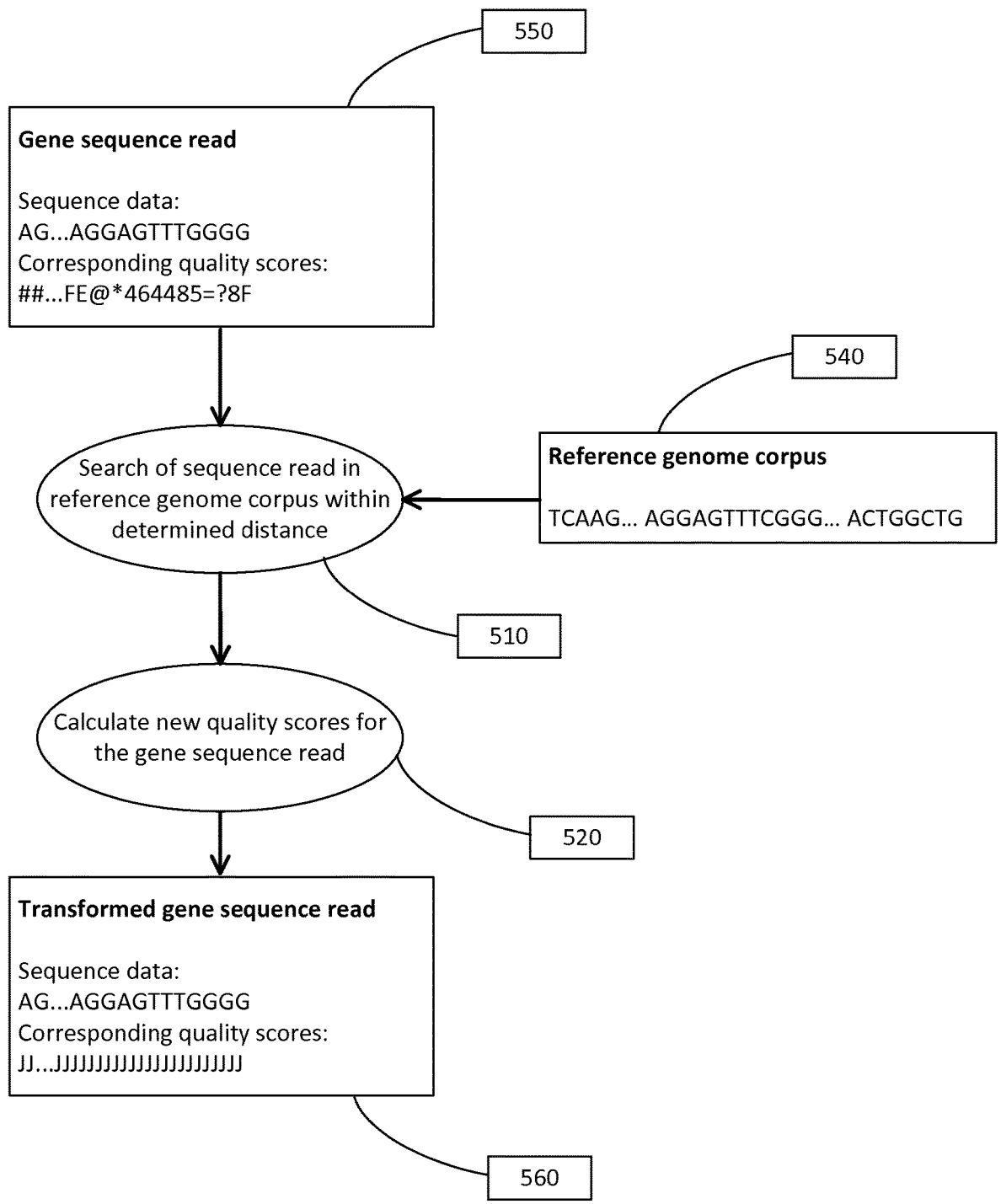
Figure 6A:
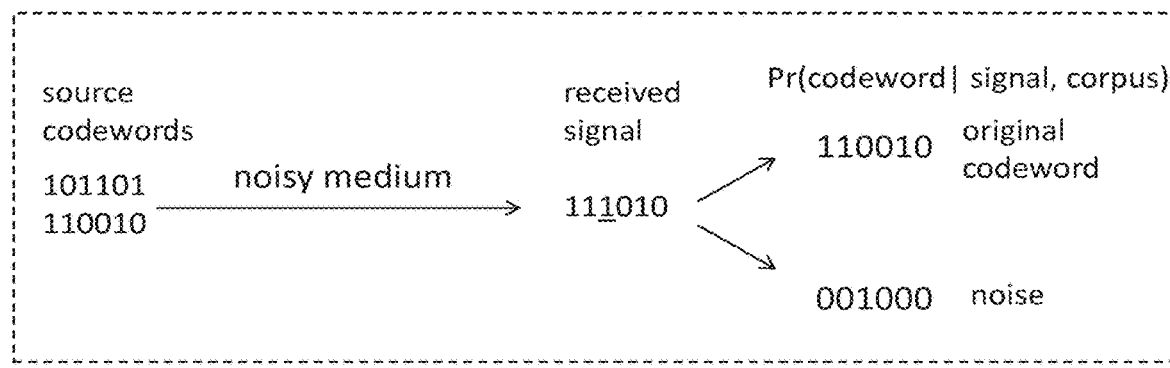
Figure 6B:
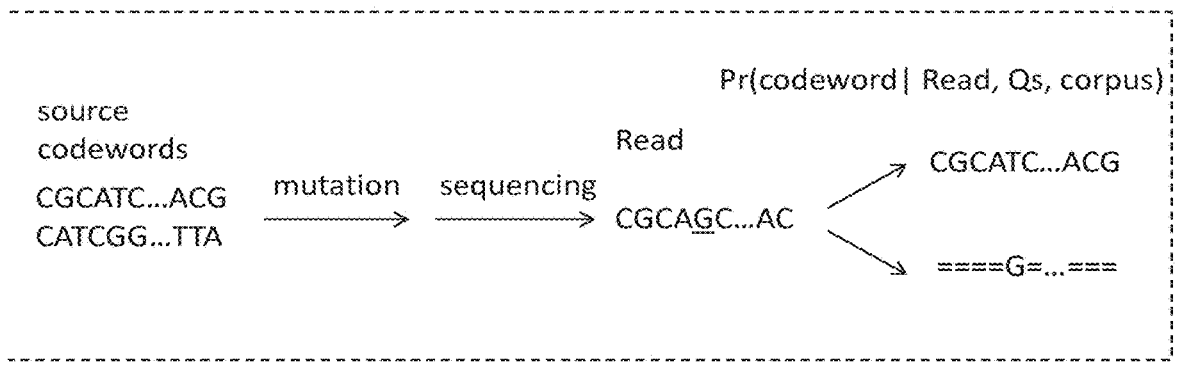
Figure 7:
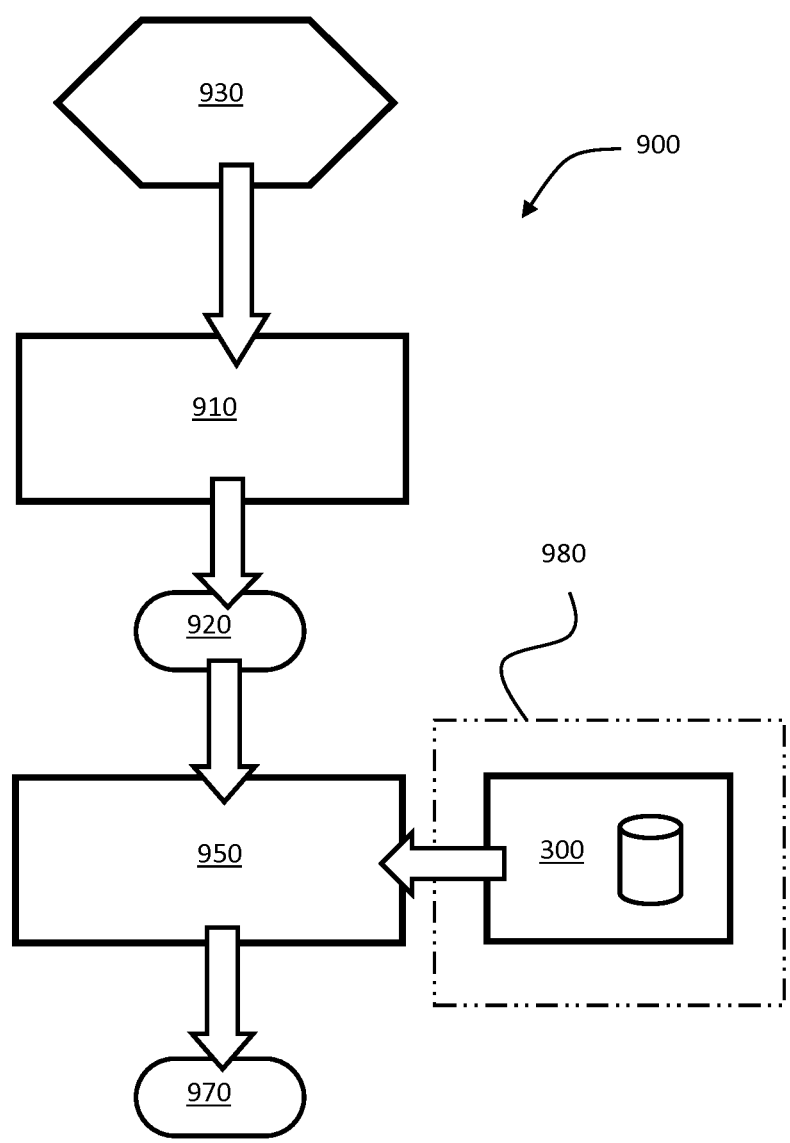

FIG. 5a and FIG. 5b are further schematic illustrations of the method according to an embodiment of the disclosure based on the corresponding methods of FIG. 3a and FIG. 3b;

FIG. 6a and FIG. 6b are schematic illustrations of the difference between Coding Theory as generally applied (FIG. 6a), and as applied according to embodiments of the present disclosure (FIG. 6b); and FIG. 7 is a schematic illustration of a system for generating genomics data pursuant to the present disclosure, wherein the system includes an apparatus for deriving genetic sequence data from a biological genetics material, for example a sample of chromosome material including deoxyribonucleic acid (DNA) or ribonucleic acid (RNA), and a data processing apparatus for processing the genetic sequence data with respect of a genetic corpus to generate corresponding output genetic sequence data, wherein the data processing apparatus is operable to employ methods of data processing pursuant to the present disclosure,

DETAILED DESCRIPTION OF EMBODIMENTS

Embodiments of the present disclosure are described below. In the following, reference is made to the human genome, but this should not be considered as limiting embodiments of the present disclosure, as principles of operation of the various embodiments of the present disclosure are equally applicable to any genome sequence, regardless of species or entity from which it is derived.

In embodiments of the present disclosure, there is employed an alternative form of data compression for genomic sequence data, wherein quality scores are modified using a robust statistical framework for preserving valuable information. A beneficial side effect of such a modification results in a reduction of quality score entropy.

An approach is adopted, in embodiments of the present disclosure, incorporating insights from Coding Theory, wherein such Coding Theory is usually used to deal with error correction of signal transmissions, is used to boost the signal of bases in, for example, High Throughput Sequencing (HTS) or NGS outputs according to a conservative prior and Bayesian model. Resultant boosted quality scores are a more accurate representation of a confidence of base calls in each read, and can be better compressed, thereby resulting in less data being generated when reading base sequences from biological genetic material. Unlike lossy compression schemes that approximate or throw out quality score information, the quality scores from the approach pursuant to the present disclosure are boosted according to a robust and conservative Coding Theory model. A side-effect is that most quality scores are thereby pushed beyond a saturation point of the aforementioned Phred scheme, resulting in higher compression ratios than have hitherto been achieved. Importantly, this Bayesian approach does not modify the quality scores of bases, unless there is a robust statistical basis for doing so. Instead, it improves the underlying quality score of the HTS data under a conservative prior, with improved compression as a side-effect; in technical effect, this corresponds to an improvement in signal-to-noise ratio (SNR) of a genomic sensing system in which the approach is employed.

In an ordinary case, Coding Theory describes how it is feasible to recover original codewords at a receiver when corresponding original codewords are communicated over a noisy communication channel to the receiver. Applying Coding Theory allows one in a practical manner, to separate out signal from noise utilising a Bayesian approach. There is used a Hamming Distance to determine a likelihood that a signal received at a given receiver corresponds to one codeword versus another codeword. The larger the Hamming Distance between all other codewords, the more likely it is that a given codeword can be recovered at the receiver and separated from noise thereat. Indeed, the ability of a codeword to tolerate and separate from noise grows exponentially with an increase in its Hamming Distance to other codewords.

One or more methods according to embodiments of the present disclosure provide improved methods of transforming quality scores of bases in genome sequence reads, in order to improve the quality and/or compressibility of corresponding data.

In various embodiments of the present disclosure, HTS (NGS) can be recast and modelled utilising Coding Theory. There is employed a transmission model that is based upon codewords originating, namely transmitted, from a reference genome corpus; for example, for humans, the reference genome corpus is optionally simply the human reference genome, but can be any other representative collection of human genomes. Moreover, in the case of humans, the reference genome corpus can optionally incorporate information about variants of the reference genome. The same considerations mentioned here would also apply for determining the reference genome corpus of any other species. In the transmission model, the codewords from the reference corpus undergo noise in a form of mutations to provide a given sample genome, which then undergoes sequencing that introduces further noise in a form of Read errors the result of which is the raw sequencing data, namely "received codewords". In this case the noisy medium has two parts, namely mutation and sequencing. In a first respect, this approach optionally ignores indels; "indels" are insertions and/or deletions as mutations or as a source of Read errors. For the human genome, a dominant source of variation is due to base changes rather than indels, and a dominant error in contemporary genetic sequencing machines is due to misread bases rather than indels. Thus, the type of noise can be considered primarily to be due to base changes; however, indels can also be handled in an extended implementation of embodiments of the present disclosure.

A Reference Genome, or corpus in general, is considered, which, due to a mutation with probability m, forms a Sample Genome; this Sample Genome is, for example, a genome of a given particular individual that is sequenced. From this Sample Genome multiple n-mers (where an n-mer is a contiguous sequence of length n) are randomly constructed which are then sequenced with an error probability $\epsilon$ to form a Read. Each of these n-mers can be cast back to an equivalent n-mer on the Reference Genome. Reference Genome n-mers can represent a collection of codewords, and a noisy medium encapsulates the errors introduced at all stages up to producing the Read. Conservative values are used for each of these stages. The noisy medium has a combined noise probability of $\mu = m + \epsilon 4/3m\epsilon$. To a first order, this combined noise probability is merely a sum of individual error processes $(m+\epsilon)$, but to a second order it can also take into account mutations that have been incorrectly sequenced as the original unmutated version.

It is feasible to construct ~3.2 billion codewords of n-mers from the ~3.2 billion bases in the human genome. If these bases were truly random, an average Hamming codeword distance would be expected to be $\frac{3}{4}n$ for any n-mer. However, the human genome is most certainly not random. To overcome such non-randomness, the treatment of nearby symbols is separated from more distant background codewords. Upon transmitting a given codeword, the probability that it would arrive as a particular codeword with Hamming Distance B is determinable using Equation 1 (Eq. 1):

$$\mu^B (1-\mu)^{n-B} \qquad \text{Eq. 1}$$

wherein:
n=a number of bases in a Read (may vary from Read to Read);
S=an n-mer Read codeword;
$R_k$=a reference n-mer codeword k;
$G_k$=a true Sample Genome n-mer codeword k;
$S_j$=a base j of n-mer Read;
$\epsilon_j$=a Read error for base j of n-mer Read;
$R_{kj}$=a base j of reference codeword k;
$G_{kj}$=a base j of true Sample Genome codeword k;
$Z_j$=a base j of true Sample Genome source codeword corresponding to the Read.—

The codeword S corresponds to an n-mer Read. Moreover, $R_k$ is generated from a reference genome by enumerating all possible n-mers from this reference. It is assumed in the following that there is a true Sample Genome that is derived from the reference genome according to a mutation process with per-base probability of mutation m. Moreover, in the following, it is assumed that $G_k$ is the matching enumeration of all possible n-mers from this Sample Genome.

Based on a Markovian mutation process M, with probability m, and Read error process E, with probability $\epsilon$, Equation 2 (Eq. 2) pertains:

$$Pr(S_j | R_{kj}) = \begin{cases} (1-m)(1-\epsilon_j) + \frac{1}{3}m\epsilon_j & \text{if } S_j = R_{kj} \\ (1-m)\epsilon_j + m(1-\epsilon_j) + \frac{2}{3}m\epsilon_j & \text{if } S_j \neq R_{kj} \end{cases} \qquad \text{Eq. 2}$$

$$Pr(S | R_k) = \prod_j Pr(S_j | R_{kj})$$

From the Bayes' theorem, there is derived Equation 3 (Eq. 3):

$$Pr(R_k | S) = \frac{Pr(S | R_k) Pr(R_k)}{\sum_i Pr(S | R_i) Pr(R_i)} \qquad \text{Eq. 3}$$

$$= \frac{Pr(S | R_k)}{\sum_i Pr(S | R_i)}$$

wherein:

$$Pr(R_k) = \frac{1}{N} \qquad \text{Eq. 4}$$

for N possible n-mers, corresponding to uniform sequencing of a genome. Moreover, given a particular $R_k$ and s, the probability that a base $S_j$ mismatches the source codeword from the Sample Genome corresponding to the Read $Z_j$, namely is a Read error, is determinable from Equation 5 (Eq. 5):

$$Pr(S_j \neq Z_j | S, R_k) = \begin{cases} \dfrac{m\epsilon_j}{3 - 3m - 3\epsilon_j + 4m\epsilon_j} & \text{if } S_j = R_{kj} \\ \dfrac{\epsilon_j(3-m)}{3\epsilon_j + 3m - 4m\epsilon_j} & \text{if } S_j \neq R_{kj} \end{cases} \quad \text{Eq. 5}$$

Then, removing the dependence on $R_k$, it is feasible to determine the Read error per base as provided by Equation 6 (Eq. 6):

$$Pr(S_j \neq Z_j | S) = \sum_k Pr(S_j \neq Z_j | S, R_k) Pr(R_k | S) \quad \text{Eq. 6}$$

$$= \frac{\sum_k Pr(S_j \neq Z_j | S, R_k) Pr(S | R_k)}{\sum_i Pr(S | R_i)}$$

With ~3.2 billion codewords, this calculation is resource intensive if completed by brute force in a data processing device. By recognising that the contribution of reference codewords decreases exponentially according to their Hamming distance from the Read codeword, this calculation can be sped up with negligible error, as will next be described.

In the following, there is used L to denote a set of local indices s.t.:

$$\forall k \in L, |R_k - S| < B \quad \text{Eq. 7}$$

$$\forall k \notin L, |R_k - S| \geq B \quad \text{Eq. 8}$$

for some Hamming Distance B. The choice of B is ideally such that:

$$\sum_{i \notin L} Pr(S | R_i) \ll m\epsilon \sum_{i \in L} Pr(S | R_i) \quad \text{Eq. 9}$$

Then:

$$Pr(S_j \neq Z_j | S) \approx \frac{\sum_{k \in L} Pr(S_j \neq Z_j | S, R_k) Pr(S | R_k)}{\sum_{i \in L} Pr(S | R_i)} \quad \text{Eq. 10}$$

There are $$3^B \binom{n}{B}$$

possible codewords $X_k$ at a distance B. To obtain an estimate $\beta$ for the background contribution, the average probability of these codewords $Pr(S|X_k)$ is normalised to N codewords, leading to a value that is typically a very large overestimate and thus conservative in practice, as given by Equation 11 (Eq. 11):

$$\beta = N\mu^B (1-\mu)^{n-B} \quad \text{Eq. 11}$$

Therefore, a conservative overestimate of each base's Read error can be represented by Equation 12 (Eq. 12):

$$Pr(S_j \neq Z_j | S) \approx \frac{\sum_{k \in L} Pr(S_j \neq Z_j | S, R_k) Pr(S | R_k) + \dfrac{\epsilon_j(3-m)}{3\epsilon_j + 3m - 4m\epsilon_j}\beta}{\sum_{i \in L} Pr(S | R_i)} \quad \text{Eq. 12}$$

This estimate of a base's Read error represents the new, boosted quality score for the base upon conversion using the Phred scheme:

$$Q = -10 \log_{10} P \quad \text{Eq. 13}$$

where Q is the Phred quality score for an error probability of P.

For each Read, the initial distance to search is dependent upon the expected error rate and the length of the Read, so that longer reads may need larger search distances. For example, there is optionally used a search distance based upon a worst case Read error $\epsilon$ plus some margin multiplier, for example $2n(\epsilon+m)$). Since the maximum width of a slot may be constrained, for example to 32 bases, this may also place a constraint on the minimum distance that can be searched; in this example case, it is $\lfloor n/32 \rfloor - 1$. Likewise, the background error may be excessive if the search distance is too low, so a minimum distance, for example a search distance of 5, may also be applied.

Moreover, the present disclosure is associated with following exemplary methods:

Method A: Codeword Search

To find all codewords with up to M mismatches from the read, the read is divided into M+1 slots. Based upon a Pigeonhole principle, for any codeword up to a Hamming distance N away, there must be one slot that does not contain a mismatch, namely is an exact match. All slots are searched for all matching codewords. If a particular slot, for example, is a n-mer, a search is made to find all codewords that contain that particular n-mer. The union of searches across the slots is then guaranteed to contain at least all those codewords within the desired Hamming distance M; however, it can also contain candidate codewords that are greater than this distance. Filtering is beneficially used to discard codewords that are greater than distance M. The per-slot search, namely a Slot LU in FIG. 1, can be achieved by first indexing the reference sequence/corpus according to overlapping n-mers as a pre-processing step; for example, if the corpus contains a sequence of bases ACGGCTAC at some position, namely a position within a reference genome, 1004, then a 6-mer index for that would contain a position 1004 at an index ACGGCT and a position 1005 at an index CGGCTA and a position 1006 at an index GGCTAC. For each slot, the set of possible matching codewords is then easily determined by looking up the index for match positions in the corpus. It will also be appreciated that the larger the slot width, the more specific the slot search, and the fewer the possible candidate codewords that need to be examined.

For performance reasons, therefore, it is desirable to have wide slots for searching. However, sometimes, more narrow slots are desired, for example when searching smaller reads or larger Hamming distances. A following flexible indexing mechanism allows such freedom of searching, namely using slots of selectable width. For each overlapping k>12 bases, a 24-bit, namely 2-bits per base, primary index is generated from the first 12 bases. For each primary index, a starting position is stored in the reference genome/corpus to the index together with a secondary index of remaining (k−12)

bases. For example, a secondary index of 8 bits enables 4 additional bases to be stored, resulting in a combined 16 base index, so that a string of bases CTATCGGCT-CACTGGA would have a primary index of CTATCGGCT-CAC and a secondary index of TGGA. Similarly, a secondary index of 32 bits enables a 28 base index, namely 12 primary+16 secondary. Within each primary index, the entries are sorted according to the secondary index. When searching a slot width of size 12 then, only the primary index is used, and all offsets are retrieved within that index. However when searching a slot width of, for example, size 15, the secondary index is also used to, via binary traversal, retrieve only those offsets that match the additional 3 bases. When searching a slot width that is greater than both the full index size, for example a size of 30 bases when only a 16 base full index is available, then this is achieved by determining the intersection of overlapping 16-base index searches; for example, a search of CTATCGGCTCACTG-GAGCTAACCGATCGAT would consist of a search of CTATCGGCTCACTGGA and GAGCTAACCGATCGAT each represented by a slot lookup search, followed by an intersection operation on results thereby obtained. Such a methodology allows for rapid and flexible searching of reads within a desired Hamming distance across the reference corpus.

A further speedup in searching can be achieved by making use of the secondary index even when the slot search width is narrow. This speedup is done by directly determining the Hamming distance from the difference between the secondary index and the corresponding section of the Read. If the Hamming distance exceeds the search distance, then it is thereby identified that this candidate codeword does not meet the search criteria and can be discarded early, rather than at the filtering stage. This early discarding saves on random accesses to the reference genome/corpus, resulting in fewer expensive cache misses. In this case, extra bases beyond the slot are also passed to the Slot LU operation, namely up to a combined size of the full index, to leverage this early filtering operation. For example, a 12-mer slot search of CTATCGGCTCAC where the full index is 20 bases and the Hamming search distance is 3, the slot search operation can be provided the extra 8 bases TGGAGCTA that immediately follow the slot search bases. When determining a list of candidates, instead of adding all items that match the 12-mer search, the secondary index of a candidate can be compared against the extra provided bases to determined whether or not it has a Hamming distance of 4 or more, and thus conditionally to exclude candidates.

Method B: Read Processing

In an event that a Read has poor quality scores, namely high errors, at the head and tail of the Read, a simple pre-processing step involves truncating the Read on both sides thereof according to a maximum tolerable quality score, for example a maximum tolerable quality score corresponding to a probability of Read error of 10% or higher. This truncated result is optionally only used for feeding into the analysis pipeline, and the original Read is not itself truncated.

Method C: Quality Score Quantisation

In embodiments of the present disclosure, boosted quality scores are optionally improved to such an extent that they represent negligible error. Such quality scores can be constrained to a maximum saturation value S, for example to a value 40, beyond which they cannot be further boosted. Those quality scores that are boosted from a value x to a non-saturation value y<S optionally, instead of recording the value y, use a quantised value y'=f(y), for example based upon the Illumina 8-bin quantisation values, provided that a condition y'>x pertains. Such an approach means that the resultant quality scores are conservatively quantised with the boosting, leading to higher compression ratios in data generated in a system for generating genomic data from samples of biological genetic material.

Method D: Edit-Distance Searches

Reads with indel, namely DNA base insertion or deletion, variants that are not present in the corpus are likely to result in large Hamming distances to the corpus. Such variants mean that it is highly unlikely for such reads to be successfully boosted, for example with reference to aforementioned Method C, thus preserving their original quality scores. It is optionally feasible to replace Hamming distance searches of a corpus with edit-distance searches instead. An edit-distance search can incorporate a model of both in-place mutations/Read-errors as well as indels. In this case, the Markov model from $R_k$ to $G_k$ optionally incorporates the in-place mutation rate $m_B$ as well as an insertion rate $m_I$ and deletion rate $m_D$ as processes. The sequencing Read error is then still based on the values from the actual Read; however, additional estimations of the sequencer insertion error rate $\epsilon_I$ and deletion rate $\epsilon_D$ are optionally incorporated as well. Edit-distances searches can be done by again utilising the aforesaid Pigeonhole principle, but this time accounting for indels as well. Systematic sequencer indels affecting a whole flow-cycle of base reads, such as for Pacific Bioscience sequencers for example, are optionally also modelled with a Bayesian approach across affected reads, or by directly incorporating flow-cycle error information into the estimated indel error rates that vary per base across the read.

Method E: Long Reads

For long reads, such as those that are thousands of bases long, it may be impractical to process the entire Read at once, so the Read itself is optionally split into smaller) sub-reads, for example fixed or variable width, that themselves may benefit from the aforementioned boosting process. The long Read is then optionally assembled from the boosted result of these sub-reads. In some conditions, this can lead to faster and better results than directly applying boosting on the long Read itself. An average amount that quality scores are boosted grows according to the length of the Read being boosted, however this also increases the probability of an indel being encountered and for Hamming-based searches can thus result in little or no boosting. Moreover, there is no advantage gained in boosting quality scores beyond the saturation threshold. Thus, a criteria for determining the split length is optionally made according to both keeping the likelihood of encountering an indel low (<1%) for each sub-read, as well as maintaining a length that ensures most quality scores in the sub-read are boosted to the saturation threshold. For searches based on edit-distance, the likelihood for encountering indels can be higher and thus longer sub-reads may still be appropriate; however, the likelihood of encountering larger indel regions or regions of structural variation may still need to be kept low.

Each of the methods A, B, C, D, and E can be used separately, or optionally in combination with each other.

Analysis Steps

Next, an analysis pipeline employed in embodiments of the present disclosure will be described in greater detail.

In the pipe-line, following steps are executed:

Step 1: A pre-processing step of taking a reference genome or other corpus to generate a (dynamic) index.

Step 2: Optionally, pre-selecting one or more success criteria to determine whether or not efforts to adjust quality scores are sufficient. These criteria optionally include, but are not limited to, a combination of one or more of the following: a proportion of quality scores that are saturated or adjusted, a slot width, a distance searched, a number of iterations searched, a background likelihood, and so forth.

Step 3: For each Read, following operations are performed:
  Step 3.1: Optionally, determining a suitable Hamming, or Edit distance, or other similarity criteria for the search. When this step is not executed, suitable fixed values can be used instead. These fixed values can represent any of the following parameters: Hamming distance, Edit distance, Slot Width, etc. Such values are not limited to these parameters and can also represent other forms of similarity criteria;
  Step 3.2: finding all codewords in the corpus within given search distance (from Step 3.1) as candidate source codewords;
  Step 3.3: using Bayes Theroem for determining a likelihood of candidate source codewords occurring;
  Step 3.4: estimating a contribution of all other background source codewords, including assuming a zero contribution;
  Step 3.5: using these estimations to calculate a new quality score per base, optionally quantizing using some predefined quantisation scheme, for example a proprietary Illumina 8-bin or other, scheme including customised variants of such quantisation schemes.
  Step 3.6: adjusting quality scores based on new calculated quality scores, for example only if a new quality score is better than the old quality score, should the quality score be replaced with the new quality score.

Step 4: Optionally, to be even more conservative and minimise any possible bias, following steps are performed:
  Step 4.1: processing all reads against a codeword set to find all positions where there are mismatches. Marking these mismatches in the codeword set, for example for a reference genome corpus, mark positions in the reference genome that correspond to mismatches; and then
  Step 4.2: then for each Read, ensuring quality scores are preserved at these mismatch positions.

Detailed Description of the Diagrams

Figure 1:
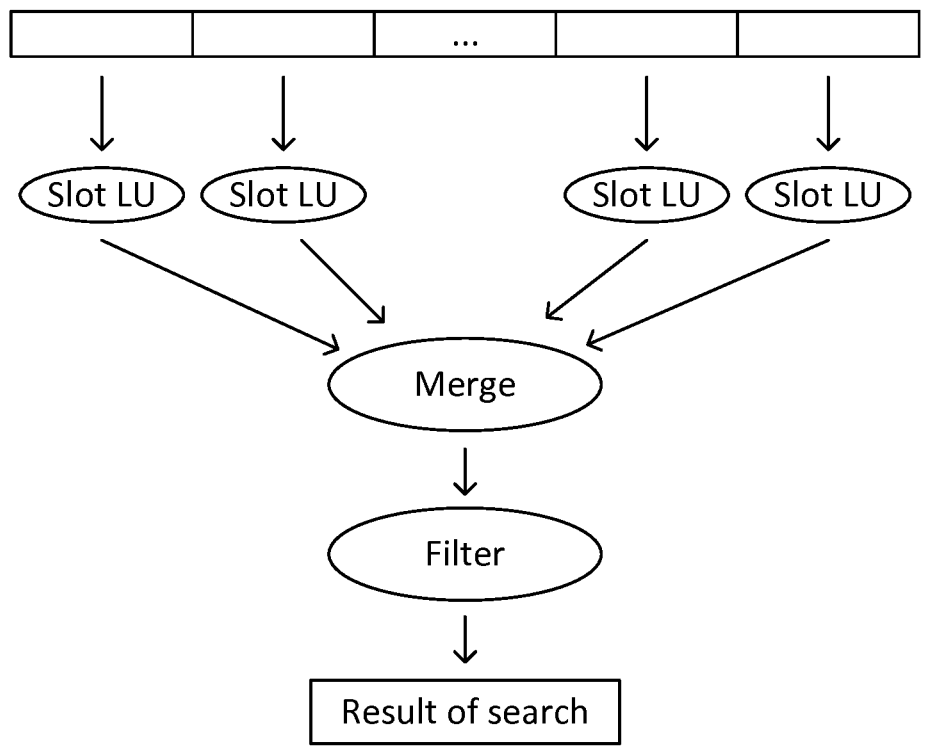
FIG. 1 is a schematic illustration of dividing a codeword search into multiple slot lookup searches.

Referring now to FIG. 1, there is shown a schematic illustration of steps in a search operation of distance up to M; the search is performed in a system pursuant to the present disclosure, wherein the system includes a genetic sequencing arrangement for deriving genetic base sequences from biological genetic material. The system includes, for example, an arrangement for cutting DNA derived from the biological genetic material into a plurality of portions, and then profiling the portions, for example by using electrophoresis optical sensing. Such cutting is, for example, achieved using specific types of enzymes or similar. Here an n-mer read is partitioned into M+1 slots, wherein each slot is looked up with a Slot LU operation, and wherein results from which are merged together to form a list of candidate codewords. This list of candidate codewords is then filtered to include only candidate codewords that are of distance less than M, which then forms a list of results.

Figure 2:
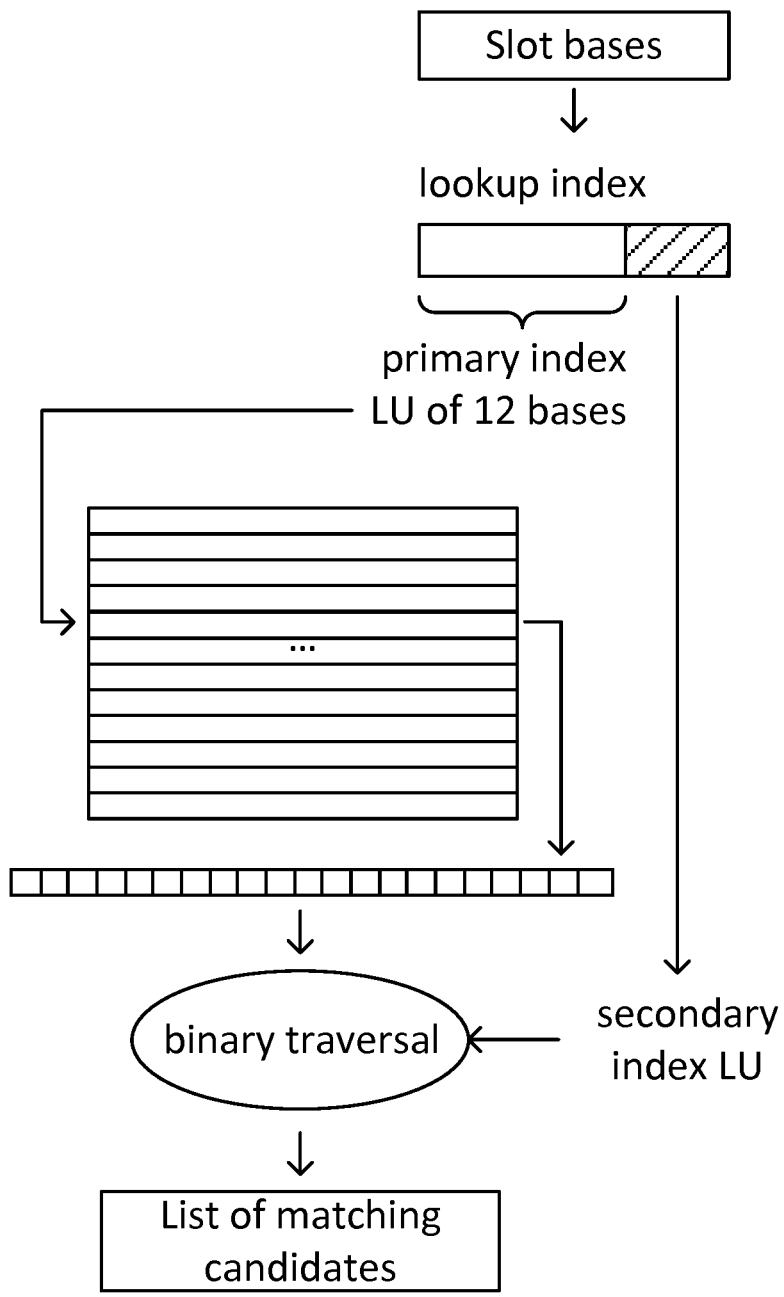
FIG. 2 is a schematic illustration of an individual slot lookup search.

Referring next to FIG. 2, there is shown an schematic illustration of the Slot LU operation from FIG. 1. Here, in FIG. 2, the input slot bases are partitioned into an input primary index and an input secondary index. The input primary index is used to lookup the primary index table to obtain a list of candidates, wherein each element in the list consists of:
  (i) an offset in the corpus corresponding to candidate codewords; and
  (ii) secondary index information.

The input secondary index is then used to do binary traversal of this list according to its secondary index information, so as to retrieve a subset of the list of candidates that match at least a portion of the input secondary index. Such retrieval can be regarded as being a link of coarse and fine filtering mechanisms.

Referring next to FIGS. 3a and 3b, there is shown a schematic illustration of a method according to an embodiment of the present disclosure. The method comprises:—
(a) a first step 300 as shown in FIG. 3a of determining a correspondence distance to search in a reference genome corpus; This step is optional and FIG. 3b shows a version of this method that does not incorporate this step.
(b) a second step 310 of performing a search of the sequence of bases in the reference genome corpus within the determined correspondence distance;
(c) a third step 320 of calculating an adjustment for each quality score of the sequence, based on results of the search; and
(d) a fourth step 330 of adjusting quality scores according to the calculation.

Referring now to FIG. 4a, there is shown a schematic illustration of a method according to an embodiment of the present disclosure. The method comprises the aforementioned steps 300, 320 and 330, as presented in FIG. 3a and detailed sub-steps that further illustrate the step 310 of FIG. 3a comprising:—
(i) a sub-step 410 of partitioning the sequence of bases into a plurality of slots;
(ii) a sub-step 420 of performing at least one lookup operation for each slot into the reference genome corpus to obtain candidate codewords; and,
(iii) a sub-step 430 of combining candidate codewords from each slot to obtain a list of results.

Referring now to FIG. 4b, there is shown a schematic illustration of a method according to an embodiment of the present disclosure. The method comprises the aforementioned steps 320 and 330, as presented in FIG. 3b and detailed sub-steps that further illustrate the step 310 of FIG. 3b comprising:—
(i) a sub-step 410 of partitioning the sequence of bases into a plurality of slots;
(ii) a sub-step 420 of performing at least one lookup operation for each slot into the reference genome corpus to obtain candidate codewords; and,
(iii) a sub-step 430 of combining candidate codewords from each slot to obtain a list of results.

Referring next to FIG. 5a, there is shown an illustration of steps of a method according to an embodiment of the disclosure, based on the method of FIG. 3a. In FIG. 5a, a first method step 500 is equivalent to the method step 300, and a first action is to determine a correspondence distance to search. A step 510 is equivalent to the method step 310. A step 520 is equivalent to a combination of the method steps 320 and 330, such that to calculate new quality scores for the gene sequence read or genomic sequence read comprises calculating an adjustment for each quality score of the sequence, based on results of the search and adjusting quality scores according to the calculation.

In FIG. 5a, there is further illustrated that the reference genome corpus 540 is optionally consulted for the step 500. The reference genome corpus 540 is consulted for the step 510 and there is also illustrated some of the bases associated with the corpus. The gene sequence read 550 is also shown comprising examples of the sequence data with associated bases and quality scores. Finally, at the end of processing involved with the method, a transformed gene sequence read 560 is obtained with adjusted quality scores. It will be appreciated that the adjusted quality scores are analogous to signal data, whose noise content has been reduced, namely has an improved analogous signal-to-noise ratio (SNR). As a result of noise reduction, genomic sequence available at the transformed gene sequence read 560 with adjusted quality scores can be more efficiently compressed without substantial loss of information.

Referring next to FIG. 5b, there is shown an illustration of steps of a method according to an embodiment of the disclosure, based on the method of FIG. 3b. This method is similar to the method shown in FIG. 5a, with the exception of step 500 which is present in FIG. 5a, but is not present in FIG. 5b. Step 500, which is equivalent to the method step 300 is optional. Determining a suitable set of correspondence distances to search can be done outside this method and these values can be used in method step 510 which is equivalent to method step 310.

FIG. 6a and FIG. 6b are illustrations of Coding Theory as normally applied, namely FIG. 6a, and as implemented according to an embodiment of the present disclosure, namely FIG. 6b. In FIG. 6a, there is shown two possible codewords 600, 610 to be transmitted over a noisy medium 620 and a received signal 630. It is possible to calculate a likelihood that this received signal 630 originated from each particular codeword 600, 610. This likelihood can be calculated by use of a Bayesian approach. If a Hamming distance between source codewords is sufficiently large, the source codeword can be recovered with very high confidence. Typically, the most likely codeword is accepted as being received. In an event that more than one codeword shares the same maximum likelihood, then the typical treatment is that errors were detected but could not be corrected.

In contradistinction, the modelling of HTS (high throughput sequencing) using Coding Theory, namely an insight of the present disclosure, is illustrated in FIG. 6b. Such usage of the Coding Theory does not comprise recovering a particular codeword, but utilizing the likelihood distribution of codewords and their corresponding noise components. This use permits a potential improvement of the quality score information describing the probability of sequencing errors to determine a conditional probability of a read error for each base, given information about the rest of the read, the unconditional read error probabilities, and a corpus of codewords 640.

Referring next to FIG. 7, there is shown a schematic illustration of a system for generating genomics data pursuant to the present disclosure; the system is indicated generally by 900. The system 900 includes a genetic reading apparatus 910 for deriving genetic sequence data 920 from a biological genetics material 930, for example a sample of chromosome material including deoxyribonucleic acid (DNA) or ribonucleic acid (RNA), and a data processing apparatus 950 for processing the genetic sequence data 920 with respect of the genetic corpus 300 to generate corresponding output genetic sequence data 970, wherein the data processing apparatus 950 is operable to employ methods of data processing pursuant to the present disclosure, as described in the foregoing, Optionally, the genetic reading apparatus 910 and the data processing apparatus 950 are mutually spatially collocated, for example within a single building, laboratory or equipment enclosure. Alternatively, the data processing apparatus 950, at least in part, or in total, is located spatially remote from the genetic reading apparatus 910. For example, the data processing apparatus 950 is implemented as a digital processing device or in a computing cloud environment, for example in association with the Internet. The data processing apparatus 950 is operable to obtain the aforementioned corpus from a database, or the corpus is stored spatially locally to the data processing apparatus 950, for example downloaded from one or more databases 980 to the data processing apparatus 950 for performing implementation of methods pursuant to the present disclosure. Downloading corpus data from the one or mores databases 980 to the data processing apparatus 950 is advantageous as frequency of database accesses is thereby reduced.

The genetic reading apparatus 910 is optionally implemented using a contemporary proprietary genetic sequencing reader, for example as manufactured by Illumina Inc. or similar. Such a proprietary genetic sequencing reader is operable to split DNA or RNA of genetic material into relatively shorter sections of DNA or RNA, for example by using selective enzymic cutting, and then fluorescent optical readout if bases of the shorter sections or DNA or RNA are then sensed using electrophoresis methods.

Such readout methods will be familiar to a person skilled in the technical art of DNA sequencing. Other approaches to DNA and RNA readout are optionally employed, for example selective reaction methods or similar to explore a manner in which DNA or RNA genetic material expresses itself when biologically transcribed.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A system for generating output genomics data from biological genetic material, wherein the system includes:
  a genetic reading apparatus which is operable to read bases included in the biological genetic material to generate a genome sequence read, wherein the genome sequence read comprises at least one sequence of bases and associated quality scores; and
  a data processing apparatus for processing the genome sequence read to generate the output genomics data, wherein the data processing apparatus is operable:
    (a) to perform a search of the at least one sequence of bases in a reference genome corpus comprising n-mers from a reference genome, based upon a similarity criterion;
    (b) to calculate an adjustment for one or more of the associated quality scores, based upon results of the search, wherein the adjustment calculation for a quality score associated with a base in the genome sequence read utilises a Bayesian estimation of a likelihood of a sequencing error at the base given the sequence of the read, wherein the Bayesian estimation utilises the results of the search, and wherein the Bayesian estimation of the likelihood of the sequencing error at the base given the sequence of the read comprises an estimation based on n-mers found in the search to satisfy the similarity criterion, and an estimation of a contribution of all other n-mers in the reference genome corpus; and (c) to adjust one or more of the associated quality scores according to the calculated adjustment from (b).

2. The system of claim 1, wherein the similarity criterion includes a correspondence distance based upon a number of bases that are different between n-mers of the reference genome corpus and the at least one sequence of bases, wherein the correspondence distance to search is a Hamming-distance or Edit-distance.

3. The system of claim 1, wherein the Bayesian estimation of the likelihood of the sequencing error at the base given the sequence of the read depends on a probability that the base is a read error given the sequence of the read and a sequence of a candidate n-mer in the reference genome corpus identified in the search, and a probability of the sequence of the read given the sequence of the candidate n-mer, wherein the probability that the base is a read error given the sequence of the read and the sequence of a candidate n-mer in the reference genome corpus identified in the search depends on the quality score associated with the base of the genome sequence read and/or on a per-base probability of a mutation between the reference genome corpus and a sample underlying the genome sequence read.

4. The system of claim 1, wherein the system is further operable:
(i) to pre-select at least one success criterion, suitable for determining whether or not adjustments to quality scores of said genome sequence read are sufficient;
(ii) to calculate at least one candidate adjustment for quality scores of the genome sequence read;
(iii) to determine if the pre-selected at least one success criterion has been met;
(iv) if the adjusted quality scores of the genome sequence read do not meet the preselected at least one success criterion, to perform given steps using different success criteria;
(v) if the adjusted quality scores of the genome sequence read meet the pre-selected at least one success criterion, to adjust the quality scores according to the calculation.

5. A device for generating output genomics data from biological genetic material, wherein the device is operable:
(i) to receive a genome sequence read, wherein the genome sequence read comprises at least one sequence of bases read from the biological genetic material and associated quality scores; and
(ii) to process the genome sequence read to generate the output genomics data, wherein the device is operable:
(a) to perform a search of the at least one sequence of bases in a reference genome corpus comprising n-mers from a reference genome, based upon a similarity criterion;
(b) to calculate an adjustment for one or more of the associated quality scores, based upon results of the search, wherein the adjustment calculation for a quality score associated with a base in the genome sequence read utilises a Bayesian estimation of a likelihood of a sequencing error at the base given the sequence of the read, wherein the Bayesian estimation utilises the results of the search, and wherein the Bayesian estimation of the likelihood of the sequencing error at the base given the sequence of the read comprises an estimation based on n-mers found in the search to satisfy the similarity criterion, and an estimation of a contribution of all other n-mers in the reference genome corpus; and (c) to adjust one or more of the associated quality scores according to the calculated adjustment from (b).

6. The device of claim 5, wherein the similarity criterion includes a correspondence distance based upon a number of bases that are different between n-mers of the reference genome corpus and the at least one sequence of bases.

7. The device of claim 6, wherein the correspondence distance to search is a Hamming-distance or Edit-distance search.

8. The device of claim 5, wherein the adjustment calculation utilises at least one of the associated quality scores of the genome sequence read and/or estimations of a mutation between the reference genome corpus and a sample underlying the genome sequence read.

9. The device of claim 5, wherein the device is further operable:
(i) to pre-select at least one success criterion, suitable for determining whether or not adjustments to quality scores of said genome sequence read are sufficient;
(ii) to calculate at least one candidate adjustment for quality scores of the genome sequence read;
(iii) to determine if the pre-selected at least one success criterion has been met;
(iv) if the adjusted quality scores of the genome sequence read do not meet the pre-selected at least one success criterion, to perform given steps using different similarity criteria;
(v) if the adjusted quality scores of the genome sequence read meet the pre-selected at least one success criterion, to adjust the quality scores according to the calculation.

10. The device of claim 5, wherein the device is operable to perform the search, wherein the device is operable:
(i) to partition the sequence of bases into a plurality of slots;
(ii) to perform at least one lookup operation for at least one slot into the reference genome corpus to obtain one or more candidate n-mers; and
(iii) to combine candidate n-mers from the at least one slot to obtain a list of results.

11. The device of claim 10, wherein the device is operable to perform partitioning by utilising a Pigeonhole Principle and to filter the list of results so as to exclude those not within the similarity criterion to search, wherein the slots are within a pre-determined range and the at least one lookup operation is performed as part of the search by utilising an index of n-mers within the reference genome corpus.

12. The device of claim 11, wherein the device is further operable:
(a) to arrange the index to comprise a primary index;
(b) to partition the at least one slot into a fixed-width primary search key and non-fixed width secondary search key during the at least one lookup operation;
(c) to perform a primary lookup by utilising the fixed-width primary search key in the primary index to obtain primary search results; and
(d) to perform a secondary lookup based on the primary search results, using the secondary search key.

13. A method of generating output genomics data from biological genetic material, wherein the method includes:
receiving, by processing hardware, a genome sequence read, wherein the genome sequence read comprises at least one sequence of bases and associated quality scores; and
using the processing hardware to process the genome sequence read to generate the output genomics data, by:

(a) performing a search of the at least one sequence of bases in a reference genome corpus comprising n-mers from a reference genome, based upon a similarity criterion;

(b) calculating an adjustment for one or more of the associated quality scores, based upon results of the search, wherein the adjustment calculation for a quality score associated with a base in the genome sequence read utilises a Bayesian estimation of a likelihood of a sequencing error at the base given the sequence of the read, wherein the Bayesian estimation utilises the results of the search, and wherein the Bayesian estimation of the likelihood of the sequencing error at the base given the sequence of the read comprises an estimation based on n-mers found in the search to satisfy the similarity criterion, and an estimation of a contribution of all other n-mers in the reference genome corpus; and (c) adjusting one or more of the associated quality scores according to the calculated adjustment from (b).

14. A computer program product comprising a non-transitory computer-readable storage medium having computer-readable instructions stored thereon, the computer-readable instructions being executable by a computerized device comprising processing hardware to execute a method as claimed in claim 13.

15. The device of claim 6, wherein the device is operable to:

determine the correspondence distance for the search in the reference genome corpus, and/or wherein the correspondence distance is dependent on an expected sequencing error rate and a length of the read.

16. The device of claim 5, wherein the Bayesian estimation of the likelihood of the sequencing error at the base given the sequence of the read depends on a probability that the base is a read error given the sequence of the read and a sequence of a candidate n-mer in the reference genome corpus identified in the search, and the probability of the sequence of the read given the sequence of the candidate n-mer.

17. The device of claim 16, wherein the probability that the base is a read error given the sequence of the read and the sequence of a candidate n-mer in the reference genome corpus identified in the search depends on the quality score associated with the base and a per-base probability of mutation.

18. The device of claim 5, wherein the calculation of the adjustment comprises the calculation of a new quality score for a base and the adjustment of a quality score comprises replacing the quality score with the new quality score if the new quality score is better than the old quality score.

19. The method of claim 13, wherein the similarity criterion includes a correspondence distance based upon a number of bases that are different between n-mers of the reference genome corpus and the at least one sequence of bases, and/or wherein the similarity criterion includes a Hamming-distance or Edit-distance between n-mers of the reference genome corpus and the at least one sequence of bases.

20. The method of claim 19, further comprising determining the correspondence distance for the search in the reference genome corpus, depending on an expected sequencing error rate and a length of the read.

21. The method of claim 13, wherein the Bayesian estimation of the likelihood of the sequencing error at the base given the sequence of the read depends on a probability that the base is a read error given the sequence of the read and a sequence of a candidate n-mer in the reference genome corpus identified in the search, and a probability of the sequence of the read given the sequence of the candidate n-mer, wherein the probability that the base is a read error given the sequence of the read and the sequence of a candidate n-mer in the reference genome corpus identified in the search depends on the quality score associated with the base and a per-base probability of mutation.

22. The method of claim 13, wherein calculating the adjustment comprises the calculation of a new quality score for a base and adjusting the quality score comprises replacing the quality score with the new quality score if the new quality score is better than the old quality score.

* * * * *

UNITED STATES PATENT AND TRADEMARK OFFICE
CERTIFICATE OF CORRECTION

| | |
|---|---|
| PATENT NO. | : 11,244,742 B2 |
| APPLICATION NO. | : 15/766305 |
| DATED | : February 8, 2022 |
| INVENTOR(S) | : Daniel Leo Greenfield et al. |

It is certified that error appears in the above-identified patent and that said Letters Patent is hereby corrected as shown below:

On the Title Page

In item (30) Foreign Application Priority Data:
Oct. 6, 2015 (GB) ............ 1517663
Should read:
Oct. 6, 2015 (GB) ............ 1517663.9

Signed and Sealed this
Thirty-first Day of May, 2022

Katherine Kelly Vidal
*Director of the United States Patent and Trademark Office*